US010238305B2

(12) United States Patent
Hingorani et al.

(10) Patent No.: US 10,238,305 B2
(45) Date of Patent: Mar. 26, 2019

(54) DYNAMIC OPERATION OF OPTICAL HEART RATE SENSORS

(71) Applicant: MICROSOFT TECHNOLOGY LICENSING, LLC, Redmond, WA (US)

(72) Inventors: Vinod L. Hingorani, Redmond, WA (US); Haithem Albadawi, Redmond, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 194 days.

(21) Appl. No.: 14/292,504

(22) Filed: May 30, 2014

(65) Prior Publication Data

US 2015/0342477 A1 Dec. 3, 2015

(51) Int. Cl.
*A61B 5/00* (2006.01)
*A61B 5/024* (2006.01)

(52) U.S. Cl.
CPC ...... *A61B 5/02416* (2013.01); *A61B 5/02438* (2013.01); *A61B 5/681* (2013.01); *A61B 5/721* (2013.01); *A61B 2560/0209* (2013.01)

(58) Field of Classification Search
CPC ... A61B 5/0059; A61B 5/0452; A61B 5/0006; A61B 5/0084; A61B 5/02416; A61B 5/0261; A61B 5/02154; A61B 5/02438; A61B 5/681; A61B 5/721
USPC ................ 600/473, 475, 476, 477, 508, 509
See application file for complete search history.

(56) References Cited

U.S. PATENT DOCUMENTS

| | | | |
|---|---|---|---|
| 5,263,486 | A | 11/1993 | Jeffreys |
| 5,807,267 | A | 9/1998 | Bryars et al. |
| 7,945,305 | B2 | 5/2011 | Aggarwal et al. |
| 8,552,871 | B2 | 10/2013 | Park et al. |
| 8,655,307 | B1 | 2/2014 | Walker et al. |
| 2005/0187446 | A1 | 8/2005 | Nordstrom et al. |
| 2005/0250997 | A1 | 11/2005 | Takeda et al. |
| 2009/0024007 | A1 | 1/2009 | Lee et al. |
| 2011/0066053 | A1 | 3/2011 | Yazicioglu |
| 2011/0098583 | A1 | 4/2011 | Pandia et al. |

(Continued)

FOREIGN PATENT DOCUMENTS

| | | |
|---|---|---|
| EP | 2612594 A2 | 7/2013 |
| EP | 2733578 A2 | 5/2014 |
| WO | 2010082748 A2 | 7/2010 |

OTHER PUBLICATIONS

Garmin (Garmin 305 Owner's Manual, https://support.garmin.com/support/manuals/manuals.faces?partNo=010-00467-00, Jul. 2008).*

(Continued)

*Primary Examiner* — Carolyn A Pehlke
(74) *Attorney, Agent, or Firm* — Alleman Hall Creasman & Tuttle LLP

(57) ABSTRACT

An optical heart rate sensor includes an optical source configured to illuminate one or more blood vessels through a user's skin, an optical sensor configured to measure reflected illumination from the blood vessels, and one or more energy storage cells. A controller operates the optical source and optical sensor at a first rate of energy consumption during a first condition, and operates the optical source and optical sensor at a second rate of energy consumption during a second condition.

16 Claims, 5 Drawing Sheets

(56) References Cited

U.S. PATENT DOCUMENTS

| | | | | |
|---|---|---|---|---|
| 2012/0274508 | A1* | 11/2012 | Brown | G04F 10/00 342/357.25 |
| 2013/0324855 | A1 | 12/2013 | Lisogurski et al. | |
| 2014/0073486 | A1 | 3/2014 | Ahmed et al. | |
| 2014/0288435 | A1* | 9/2014 | Richards | A61B 5/02427 600/479 |
| 2015/0120186 | A1* | 4/2015 | Heikes | G01C 22/006 701/468 |
| 2015/0251074 | A1* | 9/2015 | Ahmed | A61B 5/02405 700/91 |
| 2016/0081628 | A1* | 3/2016 | Melkoniemi | A61B 5/01 600/301 |

OTHER PUBLICATIONS

ISA European Patent Office, International Search Report and Written Opinion Issued in Application No. PCT/US2015/032503, dated Sep. 25, 2015, WIPO, 11 Pages.

Petelenz, et al., "Power limitations in embedded sensors impact signal acquisition and data processing strategies", In Proceeding of Position paper for the Embedded Hardware and Software Workshop, Jun. 2, 2005.

Nakano, et al., "Instantaneous Heart Rate Detection Using Short-Time Autocorrelation for Wearable Healthcare Systems", In Annual International Conference of the IEEE Engineering in Medicine and Biology Society (EMBC), Aug. 28, 2012, 4 pages.

Fingas, Jon, "TomTom's new GPS watches track your heart rate without a chest strap (update: US pricing)", http://www.engadget.com/2014/04/03/tomtom-cardio-gps-watches/, Apr. 3, 2014, 10 pages.

Goode, Lauren, "Samsung's New Gear Fit Needs to Work on the "Fit" Part", http://recode.net/2014/04/08/samsungs-new-gear-fit-needs-to-work-on-the-fit-part/, Apr. 8, 2014, 10 pages.

"Samsung Gear Fit, Gear 2 and Gear 2 Neo go on sale worldwide", NDTV Gadgets, http://gadgets.ndtv.com/others/news/samsung-gear-fit-gear-2-and-gear-2-neo-go-on-sale-worldwide-507220, Apr. 11, 2014, 3 pages.

Poeter, Damon, "Meet Simband, Samsung's Next-Gen Health Tracker", http://www.pcmag.com/article2/0,2817,2458663,00.asp, May 28, 2014, 5 pages.

IPEA European Patent Office, Second Written Opinion Issued in Application No. PCT/US2015/032503, dated May 6, 2016, WIPO, 8 Pages.

IPEA European Patent Office, International Preliminary Report on Patentability Issued in PCT Application No. PCT/US2015/032503, dated Aug. 26, 2016, WIPO, 9 pages.

* cited by examiner

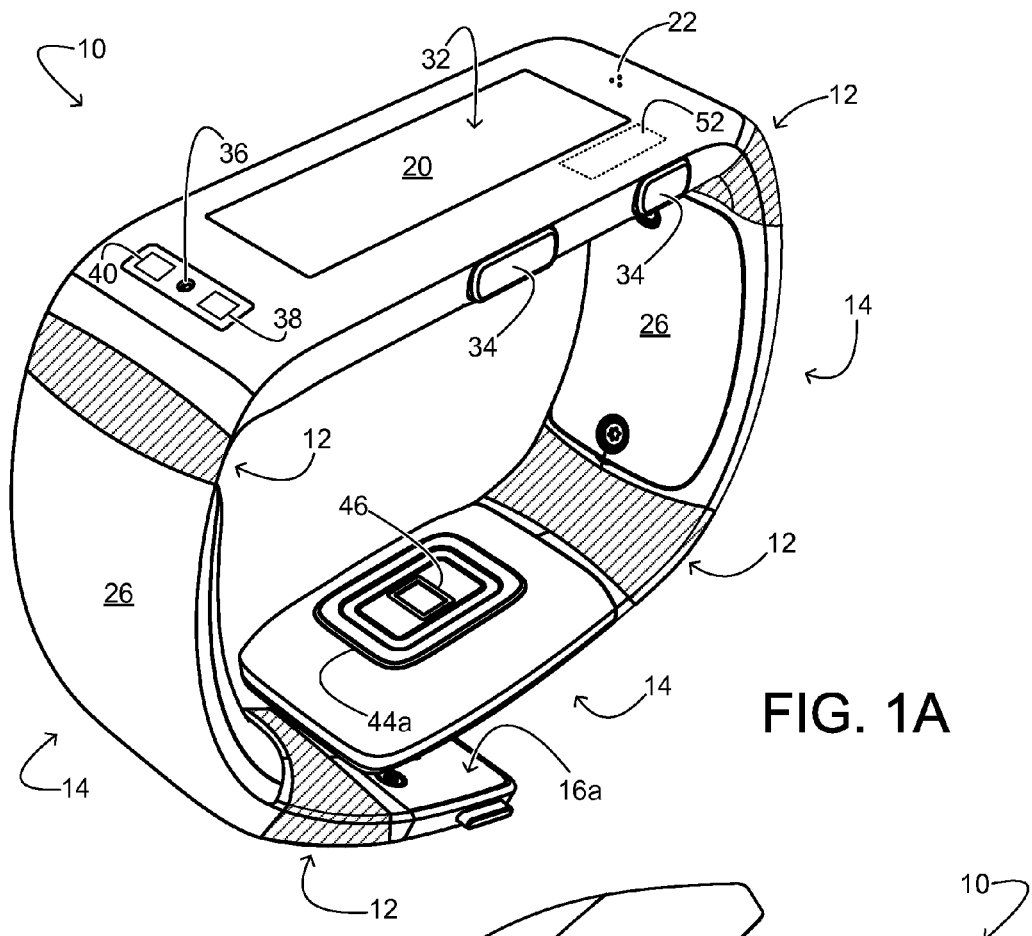
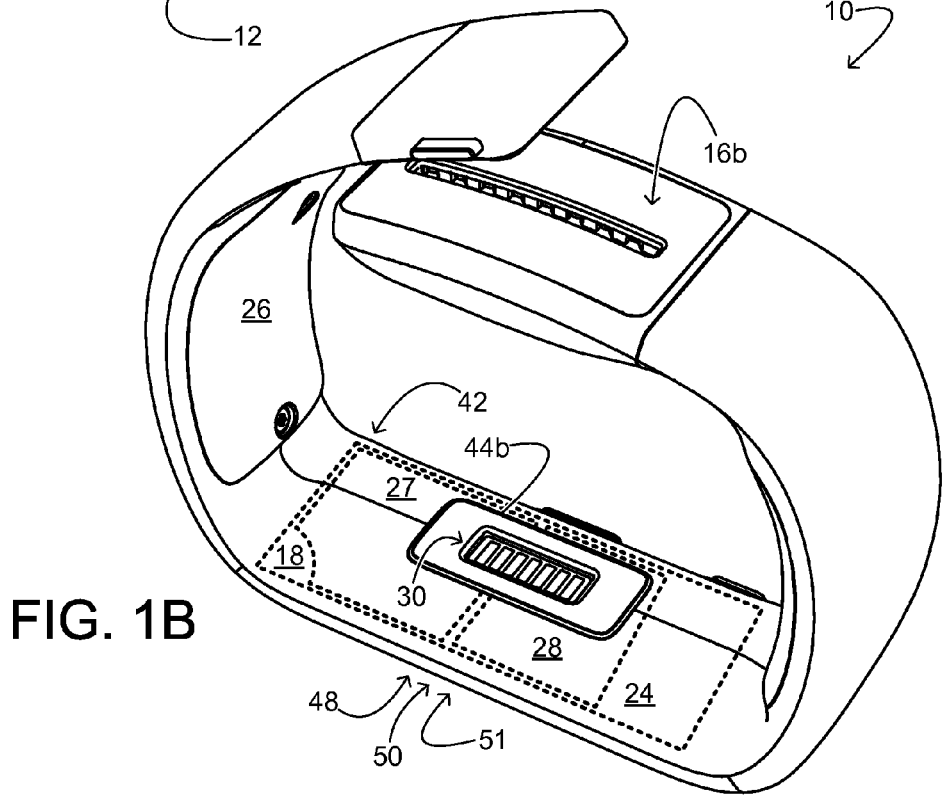
FIG. 1A
FIG. 1B

DYNAMIC OPERATION OF OPTICAL HEART RATE SENSORS

BACKGROUND

Monitoring heart rate levels provides useful health information, such as an overall fitness level. Optical heart rate sensors provide a non-invasive means of determining heart rate levels. An optical heart rate sensor may be incorporated into a wearable device.

BRIEF DESCRIPTION OF THE DRAWINGS

FIGS. 1A and 1B show a wearable electronic device.

DETAILED DESCRIPTION

Figure 2:
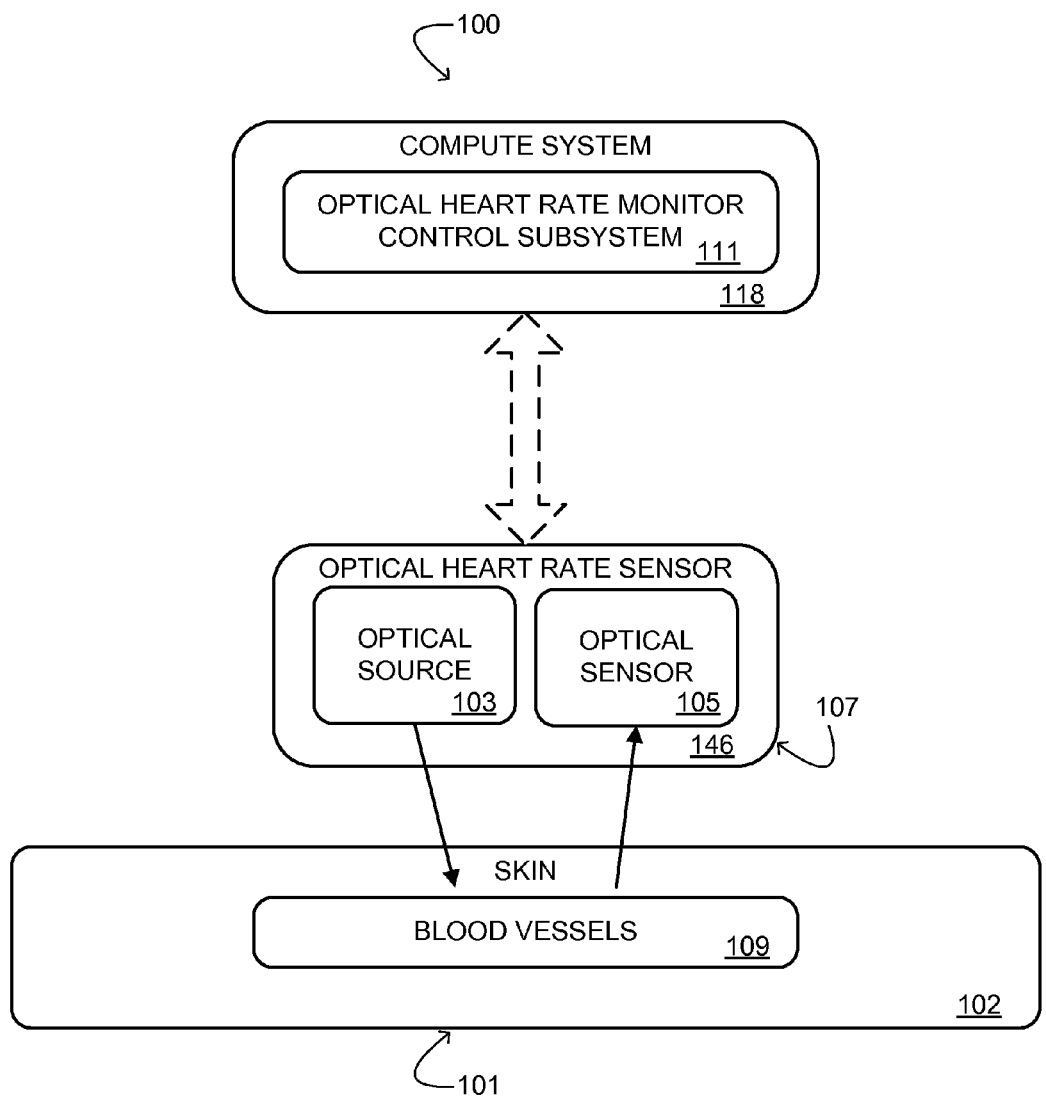
FIG. 2 schematically shows an example optical heart rate sensor that may be included in the wearable electronic device of FIGS. 1A-1B.

The present disclosure is directed to the dynamic control of the pulsation frequency of an optical source for an optical heart rate sensor. For example, the pulsation frequency of the optical source may be increased or decreased based on the quality of a signal from an optical sensor, a detected amount of motion, and/or a downstream application of a determined heart rate. While described below in the context of a wearable computing device, it is to be understood that dynamically adjusting the pulsation frequency of an optical source for an optical heart rate sensor, as described herein, may be used in numerous different applications, and with various different types of sensory-and-logic systems.

Incorporating an optical heart rate sensor into a wearable computing device allows a user to monitor health factors, such as heart rate, calories burned, response to exertion exercises, heart rate variability, etc. However, an optical heart rate sensor comprises an optical source and an optical sensor, and these components may rapidly drain the power source of the wearable computing device. To lessen power consumption, the optical source may be operated in a pulsation mode, where the source is turned on and off at a pulsation frequency. This is further advantageous if the optical sensor is maintained on, in that the optical sensor will detect ambient light when the optical source is turned off. The signal from the optical sensor may then be filtered based on the detected ambient light.

However, the signal from the optical sensor may degrade in quality with increased motion, as user motion may change the optical properties of the skin, tissues, and blood vessels beneath the optical sensor. If the pulsation frequency of the optical source is too low, this may lead to aliasing frequencies in the range of the user's heart rate, rendering the heart rate data inaccurate. In order to strike a balance between favorable power consumption and sensor accuracy, the pulsation frequency of the optical source may be dynamically controlled. For example the pulsation frequency may be increased with increased motion, and/or when a downstream application of the determined heart rate is critical, and decreased with decreased motion, and/or when the determined heart rate is to be used for a non-critical application.

In one example, an optical heart rate sensor may comprise an optical source configured to illuminate one or more blood vessels through a user's skin, an optical sensor configured to measure reflected illumination from the blood vessels, and one or more energy storage cells. The sensor may further comprise a storage machine holding instructions executable by a logic machine to operate the optical source and optical sensor at a first rate of energy consumption during a first condition, and to operate the optical source and optical sensor at a second rate of energy consumption during a second condition. By dynamically changing the rate of energy consumption based on the operating condition, the optical heart rate sensor may provide accurate data for critical applications or during times of high user activity, but will not consume power unnecessarily during times of low user activity or for non-critical applications.

FIGS. 1A and 1B show aspects of an example sensory-and-logic system in the form of a wearable electronic device 10 that includes an optical heart rate sensor 46. The illustrated device is band-shaped, with at least four flexion regions 12 linking less flexible regions 14. The flexion regions may be elastomeric in some examples. Fastening componentry 16A and 16B is arranged at both ends of the device. The flexion regions and fastening componentry enable the device to be closed into a loop and to be worn on a user's wrist. In other implementations, wearable electronic devices of a more elongate band shape may be worn around the user's bicep, waist, chest, ankle, leg, head, or other body part. The device, for example, may take the form of eye glasses, a head band, an arm-band, an ankle band, a chest strap, or an implantable device to be implanted in tissue.

Wearable electronic device 10 includes various functional components integrated into regions 14. In particular, the electronic device includes a compute system 18, display 20, loudspeaker 22, communication suite 24, and various sensors, including optical heart rate sensor 46. These components draw power from one or more energy-storage cells 26. A battery—e.g., a lithium ion battery—is one type of energy-storage cell suitable for this purpose. Examples of alternative energy-storage cells include super- and ultra-capacitors. In devices worn on the user's wrist, the energy-storage cells may be curved to fit the wrist, as shown in the drawings.

In general, energy-storage cells 26 may be replaceable and/or rechargeable. In some examples, recharge power may be provided through a universal serial bus (USB) port 30, which includes a magnetic latch to releasably secure a complementary USB connector. In other examples, the energy storage cells may be recharged by wireless inductive or ambient-light charging. In still other examples, the wearable electronic device may include electro-mechanical componentry to recharge the energy storage cells from the user's adventitious or purposeful body motion. For example, batteries or capacitors may be charged via an electromechanical generator integrated into device 10. The generator may be turned by a mechanical armature that turns while the user is moving and wearing device 10.

In wearable electronic device 10, compute system 18 is situated below display 20 and operatively coupled to the display, along with loudspeaker 22, communication suite 24, and the various sensors. The compute system includes a data-storage machine 27 to hold data and instructions, and a logic machine 28 to execute the instructions. Aspects of the compute system are described in further detail with reference to FIGS. 2 and 5.

Display 20 may be any suitable type of display. In some configurations, a thin, low-power light emitting diode (LED) array or a liquid-crystal display (LCD) array may be used. An LCD array may be backlit in some implementations. In other implementations, a reflective LCD array (e.g., a liquid crystal on silicon, LCOS array) may be frontlit via ambient light. A curved display may also be used. Further, AMOLED displays or quantum dot displays may be used.

Communication suite 24 may include any appropriate wired or wireless communications componentry. In FIGS. 1A and 1B, the communications suite includes USB port 30, which may be used for exchanging data between wearable electronic device 10 and other computer systems, as well as providing recharge power. The communication suite may further include two-way Bluetooth, Wi-Fi, cellular, near-field communication, and/or other radios. In some implementations, the communication suite may include an additional transceiver for optical, line-of-sight (e.g., infrared) communication.

In wearable electronic device 10, touch-screen sensor 32 is coupled to display 20 and configured to receive touch input from the user. The touch sensor may be resistive, capacitive, or optically based. Pushbutton sensors may be used to detect the state of push buttons 34, which may include rockers. Input from the pushbutton sensors may be used to enact a home-key or on-off feature, control audio volume, turn the microphone on or off, or other function.

FIGS. 1A and 1B show various other sensors of wearable electronic device 10. Such sensors include microphone 36, visible-light sensor 38, ultraviolet sensor 40, and ambient temperature sensor 42. The microphone provides input to compute system 18 that may be used to measure the ambient sound level or receive voice commands from the wearer. Input from the visible-light sensor, ultraviolet sensor, and ambient temperature sensor may be used to assess aspects of the wearer's environment—i.e., the temperature, overall lighting level, and whether the wearer is indoors or outdoors.

FIGS. 1A and 1B show a pair of contact sensor modules 44A and 44B, which contact the wearer's skin when wearable electronic device 10 is worn. The contact sensor modules may include independent or cooperating sensor elements, to provide a plurality of sensory functions. For example, the contact sensor modules may provide an electrical resistance and/or capacitance sensory function, which measures the electrical resistance and/or capacitance of the wearer's skin. Compute system 18 may use such input to assess whether or not the device is being worn, for instance. In some implementations, the sensory function may be used to determine how tightly the wearable electronic device is being worn. In the illustrated configuration, the separation between the two contact-sensor modules provides a relatively long electrical path length, for more accurate measurement of skin resistance. In some examples, a contact sensor module may also provide measurement of the wearer's skin temperature. Arranged inside contact sensor module 44B in the illustrated configuration is the optical heart rate sensor 46. The optical heart rate sensor may include an optical source and matched optical sensor to detect blood flow through the capillaries in the skin and thereby provide a measurement of the wearer's heart rate, blood oxygen level, blood glucose level, or other biomarkers with optical properties. Further details regarding the optical heart rate sensor, optical source, and optical sensor are provided with reference to FIG. 2.

Wearable electronic device 10 may also include motion sensing componentry, such as an accelerometer 48, gyroscope 50, and magnetometer 51. The accelerometer and gyroscope may furnish inertial and/or rotation rate data along three orthogonal axes as well as rotational data about the three axes, for a combined six degrees of freedom. This sensory data can be used to provide a pedometer and/or calorie-counting function, for example. Data from the accelerometer and gyroscope may be combined with geomagnetic data from the magnetometer to further define the inertial and rotational data in terms of geographic orientation. The wearable electronic device may also include a global positioning system (GPS) receiver 52 for determining the wearer's geographic location and/or velocity. In some configurations, the antenna of the GPS receiver may be relatively flexible and extend into flexion regions 12.

Compute system 18, via the sensory functions described herein, is configured to acquire various forms of information about the wearer of wearable electronic device 10. Such information must be acquired and used with utmost respect for the wearer's privacy. Accordingly, the sensory functions may be enacted subject to opt-in participation of the wearer. In implementations where personal data is collected on the device and transmitted to a remote system for processing, that data can be anonymized. In other examples, personal data may be confined to the wearable electronic device, and only non-personal, summary data transmitted to the remote system.

FIG. 2 shows a schematic depiction of a sensory-and-logic system 100 coupled to the wrist of a user 101 so that an optical heart rate sensor 146 is adjacent to the skin 102 of user 101. Optical heart rate sensor 146 comprises an optical source 103 configured to illuminate one or more blood vessels through the skin of the user, and an optical sensor 105, configured to measure reflected illumination from the blood vessels. Optical source 103 may comprise one or more LED emitters, for example, while optical sensor 105 may comprise one or more photodiodes matched to detect light at frequencies that are based on the frequencies of light output by the optical source. Optical heart rate sensor 146 may be coupled within a housing 107 configured to promote contact between sensor 146 and skin 102, and further configured to block, filter, or otherwise limit ambient light from reaching the optical sensor. In this way, the majority of light reaching optical sensor 105 may be light originating from optical source 103 that has reflected off of blood vessels 109 beneath skin 102. As an example, FIG. 1A shows a wearable electronic device 10 that is configured to position optical heart rate sensor 46 such that its optical source may illuminate capillaries located beneath the skin of the user's forearm while the wearable electronic device is worn by the user. In other configurations, an optical heart rate sensor may be positioned within a wearable electronic device such that an optical source illuminates a radial artery through the skin of the user while the wearable electronic device is worn by the user. Alternatively, an optical heart rate sensor and its associated compute system may be housed separately and configured to communicate via a communication suite. For example, an optical heart rate sensor may be included in a head set and configured to illuminate capillaries located in the user's ear lobe while the head set is worn by the user. An optical sensor may be configured to sense light reflected off of blood vessels located beneath the skin of the user (e.g., wrist worn), or the optical sensor may be configured to sense light transmitted through blood vessels located beneath the skin of the user (e.g., ear worn).

Compute system 118 may comprise optical heart rate sensor control subsystem 111. Optical heart rate sensor control subsystem 111 may provide control signals to optical source 103 and optical sensor 105. Optical heart rate sensor control subsystem 111 may receive raw signals from optical sensor 105, and may further process the raw signals to determine heart rate, caloric expenditures, etc. Processed signals may be stored and output via compute system 118. Control signals sent to optical source 103 and optical sensor 105 may be based on signals received from optical sensor 105, one or more motion sensors, ambient light sensors, information stored in compute system 118, input signals, user settings, clock signals, and other signals. Recent data received from optical sensor 105 may be stored in a first-in, first-out rolling buffer. Rolling buffers may also be maintained for recent data received from other sensors (e.g. motion sensors), for processed data (e.g. recent heart rates), etc. Control signals provided to optical source 103 and optical sensor 105 may be based on the data stored in the rolling buffers.

Figure 3A:
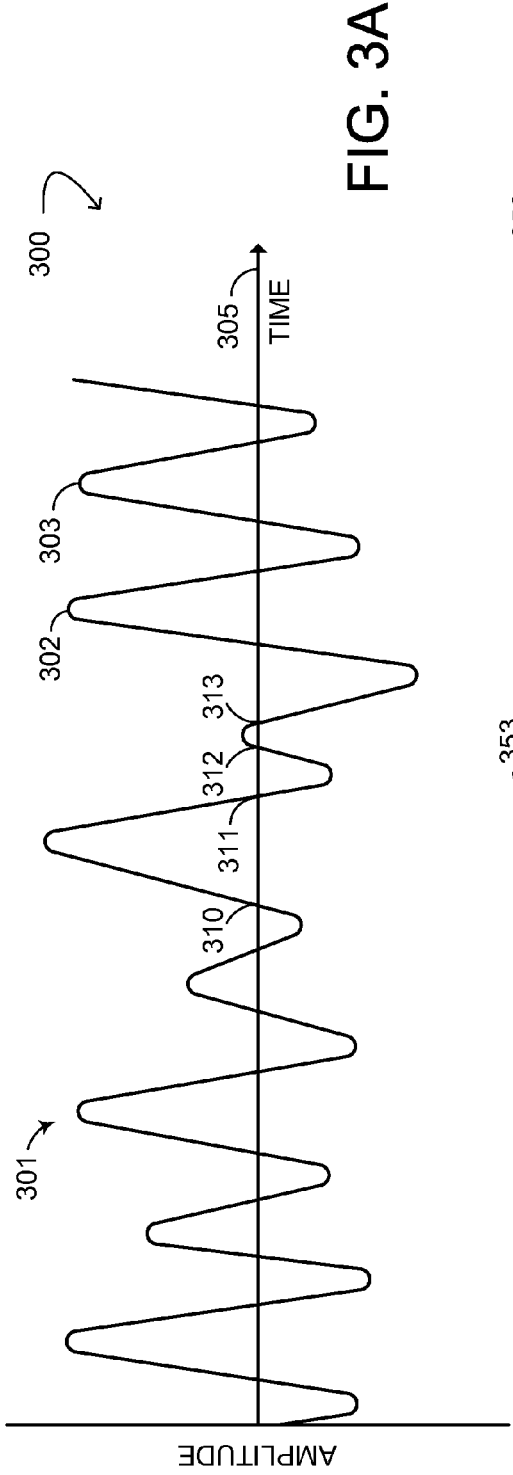
FIGS. 3A and 3B show example data traces output by an optical heart rate sensor.

FIG. 3A shows an example chart 300 of data that may be output from optical sensor 105. Chart 300 includes plot 301, indicating the amplitude of a signal received from optical sensor 105 over time. The movement of blood through the blood vessels causes the blood vessels to expand and contract, thus causing a change in the optical properties of the user's skin. The color of blood also changes across the heart beat cycle, as newly pumped blood contains more oxygen, and thus has a different absorption spectrum than blood exiting the local blood vessels. The repetitive nature of the heart beat yields a periodic plot when illuminated by an optical source. Each successive heart beat yields an amplitude peak, such as amplitude peaks 302 and 303. The length of time between peaks may thus be used to determine a heart rate. Raw data may be filtered and processed to smooth the data, and a threshold amplitude may be determined to eliminate the selection of false peaks.

As the amplitude of the peaks may change from beat to beat, heart rate may be calculated by other methods, alternatively or in addition to peak detection. For example, a zero-axis 305 may be determined and applied to the data. Each heart beat thus comprises two zero-crossing events, a negative-to-positive zero-crossing event, such as zero-crossing events 310 and 312, and a positive-to-negative zero-crossing event, such as zero-crossing events 311 and 313. As such, the length of time between alternating zero-crossing events, such as zero-crossing events 310 and 312 or 311 and 313, may be used to determine a heart rate.

Figure 3B:
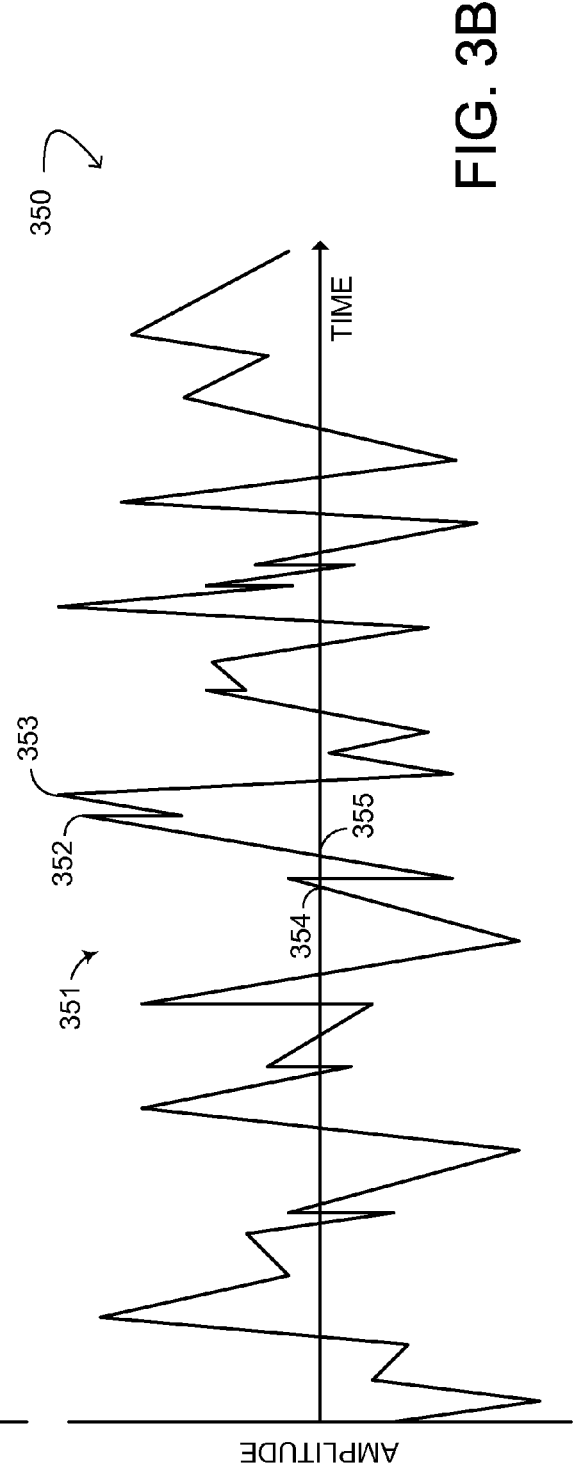

The example data shown in chart 300 has a high signal to noise ratio that provides easily-discernible peaks and zero-crossing events. However, data output from optical sensor 105 may be more complex. FIG. 3B shows an example chart 350 of data that may be output from optical sensor 105. Chart 350 includes plot 351, indicating the amplitude of a signal received from optical sensor 105 over time. Plot 351 has a lower signal to noise ratio than plot 310. Numerous factors may contribute to the addition of noise to the output of optical sensor 105. User motion may contribute to the moving of fluid through and near blood vessels that may not be discernible from blood flow driven by heart beats. If optical heart rate sensor housing 107 has poor contact with the skin of the user, the amount of ambient light reaching optical sensor 105 may change, increasing the signal-to-noise ratio. Similarly, if optical sensor 105 is seated improperly within optical heart rate sensor housing 107, signal-to-noise ratio may be increased over a properly seated optical sensor. Skin color may inherently alter light transmitted to the optical sensor, as darker colored skin is less optically transmissive than lighter skin.

With a decreased signal to noise ratio, peaks and zero-crossing events may emerge that are due to user motion or other factors, rather than user heart beats. As an example, user motion may give rise to erratic, high frequency signals that are outside the range of normal heart rates. For example, multiple peaks, such as peaks 352 and 353 along with multiple zero-crossing events, such as zero-crossing events 354 and 355 may emerge over the course of a single heart beat.

Signals received from motion sensors and ambient light sensors may be used to filter raw data output from optical sensor 105 prior to determining heart rates. Further, optical source 103 may be operated in a pulsed-on mode, as opposed to a continuously-on mode. In this way, if optical sensor 105 is operated in a continuously-on mode while optical source 103 is pulsed on and off, optical sensor 105 will detect ambient light when the optical source is off. The ambient light detected may be subtracted from, or otherwise used to smooth the raw signal from optical sensor 105.

Operating optical source 103 in a pulsed-on mode has an additional advantage in that optical source 103 consumes less power in a pulsed-on mode than in a continuously-on mode. As the optical heart rate sensor may derive power from an energy storage cell, it is advantageous to limit the power consumed with a reduced rate of energy consumption when possible. In this way, the life of the energy storage cell may be elongated while the optical heart rate sensor provides accurate data about the user's heart rate.

However, operating the optical source in a pulsation mode as opposed to an always-on mode may result in aliasing when user motion distorts the optical sensor output with high-frequency noise. Noise frequencies may thus be indistinguishable from heart rate derived signals, resulting in inaccurate heart rate calculations. Aliasing may be significantly reduced by operating the optical source at a high pulsation frequency, but this would mitigate some of the energy savings provided from operating in a pulsed mode. Rather, it may be advantageous to operate the optical source at a high pulsation frequency under certain conditions and at a lower pulsation frequency under other conditions. In other words, the optical heart rate sensor may be configured to increase or decrease the rate of energy consumption during certain conditions. For example, the optical heart rate sensor may be configured to, during a first condition, operate the optical source and optical sensor at a first rate of energy consumption; and during a second condition, operate the optical source and optical sensor at a second rate of energy consumption.

Figure 4:
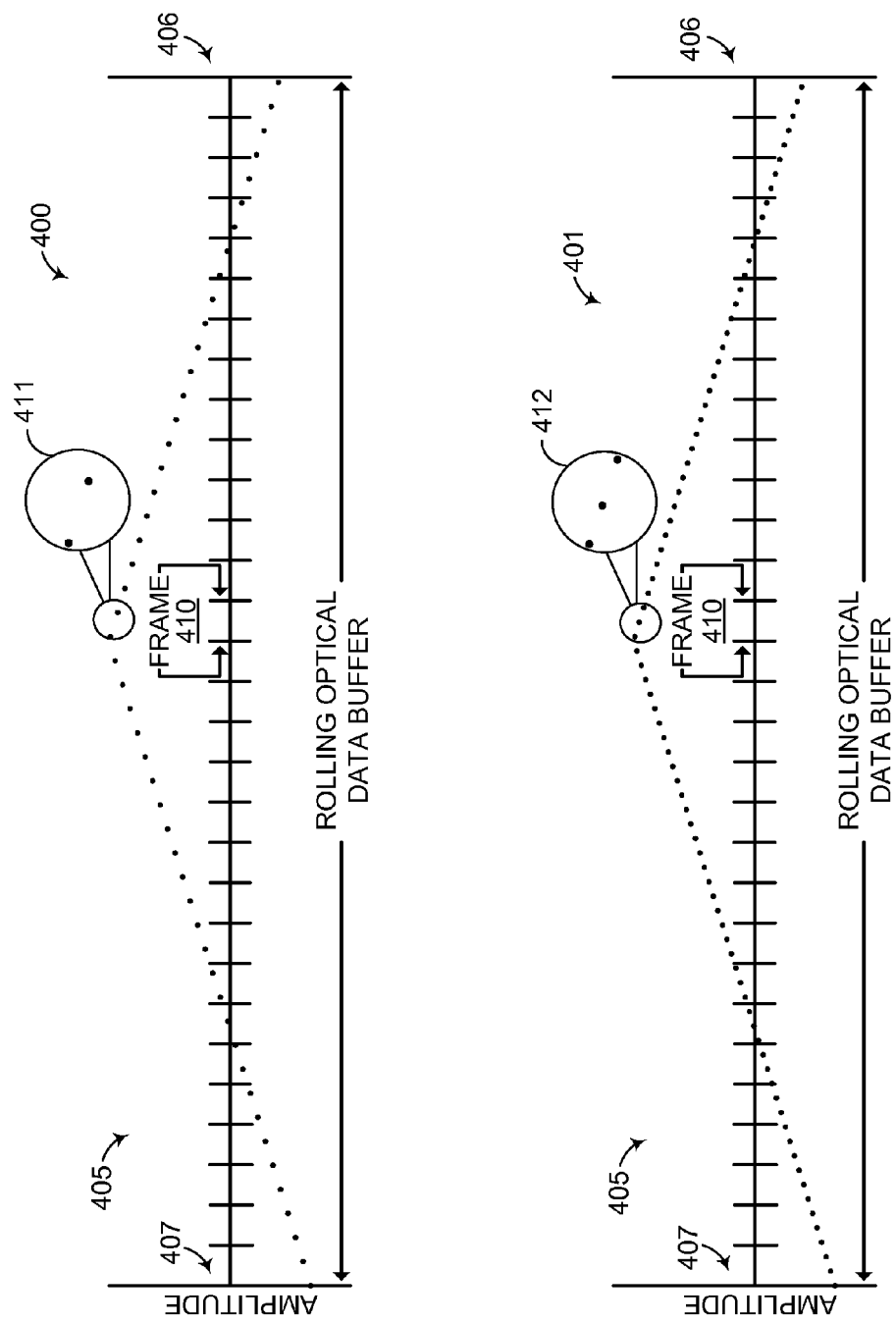
FIG. 4 shows example rolling buffers of data output by an optical hear rate sensor with an optical source configured to operate at variable pulsation frequencies.

FIG. 4 shows example data plots 400 and 401 indicating data output by optical sensor 105 with a first and second rate of energy consumption. In this example, the pulsation frequency of optical source 103 is increased from plot 400 to plot 401, increasing the rate of energy consumption.

Plot 400 schematically shows a first-in, first-out rolling buffer 405 of optical data received from optical sensor 105, where the most recent acquired data is added to rolling buffer 405 at 406. As new data is added to the rolling buffer at 406, the oldest stored data (at 407) is removed from the rolling buffer. In this example, rolling buffer 405 comprises thirty frames 410 of data. Each frame of data represents 16 ms of real time, thus giving rolling buffer 405 a total of 480 ms of data. Other durations for frames and rolling buffers may be used. Although the duration that the rolling buffer records is constant in this example, the number of data points in the buffer may increase depending on the pulsation frequency of optical source 103 within each frame. In other examples, the rolling buffer could record data over a variable duration, for example, for a predetermined number of data points. The rolling buffer could also be variably and/or dynamically sized, based on available resources such as computing power, memory, data-storage availability, etc., based on an application of the heart rate data, or other factors.

For rolling buffer 405, with a 16 ms frame length, one pulsation per frame would yield a pulsation frequency of 60 Hz. As a human heart beat will typically vary from 1-4 Hz, a 60 Hz pulsation frequency may be sufficient to derive an accurate heart beat if the signal-to-noise ratio is high, such as for the plot depicted in FIG. 3A. Such a pulsation frequency may be used, for example, to monitor a user's heart rate while sleeping. However, when the signal-to-noise ratio increases, such as for the plot depicted in FIG. 3B, the pulsation frequency may be increased to account for potential artifacts and to avoid aliasing. For plot 400, the pulsation frequency is set at 2 pulses/frame, or 120 Hz (see inset 411). Plot 401 depicts the same rolling buffer 405 as plot 400, but here, the pulsation frequency is set at 3 pulses/frame, or 180 Hz (as shown in inset 412). Thus, plot 401 depicts data output from optical sensor 105 when optical source 103 is configured to pulse on and off at a higher pulsation frequency, and thus at a greater rate of energy consumption than for plot 400.

In order to balance power consumption and the accuracy of optical heart rate sensor 146, the pulsation frequency of optical source 103 may be dynamically adjusted. The pulsation frequency may be set to a default frequency based on optimal power consumption, based on habits of the user, etc. A higher default pulsation frequency may be set for a user with dark colored skin as compared to a user with light colored skin. The pulsation frequency may be dynamically adjusted responsive to a signal received from one or more sensors. For example, the pulsation frequency may be dynamically adjusted responsive to a signal-to-noise ratio derived from a signal received from the optical sensor. The pulsation frequency may be adjusted continuously based on the signal-to-noise ratio, or may be increased responsive to the signal-to-noise ratio increasing above a threshold, and/or decreased responsive to the signal-to-noise ratio decreasing below a threshold. In this way, as the signal-to-noise ratio changes, the pulsation frequency of the optical source may be adjusted accordingly. A high pulsation frequency, and thus a high rate of energy consumption may be commanded only under certain conditions, thus decreasing overall energy consumption while maintaining the accuracy of the optical heart rate sensor.

In another example, the pulsation frequency of the optical source may be dynamically adjusted responsive to a signal received from one or more motion sensors, such as accelerometer 48, gyroscope 50, and magnetometer 51 of FIG. 1B. As described herein, an increased amount of motion may lead to signal artifacts, due to changes in the optical properties of the skin and blood vessels of the user, and/or due to changes in ambient light detected by optical sensor 105. The pulsation frequency may be adjusted continuously based on the amount of motion, or may be increased responsive to the signal-to-noise ratio increasing above a first threshold, and/or decreased responsive to the signal-to-noise ratio decreasing below a second threshold, the second threshold being lower than the first threshold. For example, if a user is moving quickly and vigorously, the pulsation frequency may be increased. Similarly, if the user is stationary or moving slowly, the pulsation frequency may be decreased.

In another example, the pulsation frequency of the optical source may be dynamically adjusted based on a downstream application of the determined heart rate. For example, if the determined heart rate measurements are being used for an application critical to the user's health, such as tracking heart rate variability for the detection of heart beat irregularities, the pulsation frequency may be increased. In another example, if the determined heart rate measurements are used to track heart rate for a burst-exertion exercise, such as sprinting, in which the data collection window is relatively short, the pulsation frequency may be increased. If the determined heart rate measurements are to be used to determine calories burned over a long-distance run, the pulsation frequency may be increased slightly over the default pulsation frequency, but may not be increased as much as for higher priority applications.

Conversely, sampling rate may be decreased for non-critical applications. For example, if the determined heart rate measurements are to be used for caloric burn rates over a full day where the user's movements are minimal, the pulsation frequency may be decreased. If the heart rate measurements are to be used to monitor heart rate while the user is sleeping, the pulsation frequency may be decreased. In this way, the pulsation frequency may be selected based on the downstream application of the heart rate measurement.

The downstream application of the determined heart rate may be selected based on user input. For example, the user may select a particular application or request particular data over a period of time, such as a programmed workout. A user may select a sprinting workout, and the pulsation frequency may increase as each sprint begins, and then may decrease some time period after each sprint ends. Additionally or alternatively, the downstream application of the determined heart rate may be selected based on signals derived from one or more sensors. For example, if signals derived from one or more motion sensors indicate that the user has made minimal movement over a period of time, the optical heart rate sensor control subsystem may infer that the user is asleep, and select a downstream application accordingly. In another example, if signals derived from the one or more motion sensors indicate a user is engaged in a particular physical activity, a downstream application may be selected based on previously determined user preferences for that particular physical activity. In another example, the user may control the pulsation frequency directly by user input, or may be able to create user-defined pulsation frequency profiles according to time and/or detected activity as determined by sensor data.

Although the above examples describe changing the pulsation frequency of an optical source as a means of changing from one rate of energy consumption to another, other means of increasing or decreasing energy consumption of the heart rate sensor may be applied. For example the optical source may be configured to pulse on and off with a pulse-on duration and a pulse-off duration as well as a pulse frequency. An increased pulse-on duration (i.e., duty cycle) may correspond with an increased rate of energy consumption. In this way, a longer total pulse-on duration may be achieved without further increasing the pulsation frequency.

In another example, the optical source may be configured to emit light with a variable light intensity. An increased light intensity may correspond with an increased rate of energy consumption. In this way, if poor data is received from the optical sensor due to the sensor being improperly seated, light intensity from the optical source may be increased, thereby increasing the ratio of optical source light to ambient light. In this way, it may be possible to increase the accuracy of determined heart rate data without increasing (or without further increasing) the pulsation frequency or pulse-on duration of the optical source.

The examples described herein have been described for examples where the optical sensor is operated in a continuously-on mode, but the optical sensor may also be operated in a pulsed-on mode at a pulsation frequency. The optical sensor pulsations may overlap with the optical source pulsations so that the reflected illumination is received by the sensor. The optical sensor pulsations may have a longer pulsation duration than the optical source pulsations, or maintain the optical sensor on for at least a portion of the pulse-off duration of the optical source. In this way, the optical sensor may sense ambient light without sensing light emitted from the optical source. The sensed ambient light may then be subtracted from or otherwise used to filter or smooth the output signal of the optical sensor. The optical source and optical sensor may be operated at first and second pulsation frequencies. The first and second pulsation frequencies may be concurrently increased or decreased responsive to signals received from one or more sensors, such as a motion sensor, and/or concurrently increased or decreased based on a downstream application of the heart beat data derived from signals output from the optical sensor. Further, the first and second pulsation frequencies may be concurrently increased or decreased responsive to an increase or decrease in a signal-to-noise ratio derived from the signal received from the optical sensor.

Accordingly, the optical heart rate sensor may be operated during a first condition at a first rate of energy consumption and operated during a second condition at a second rate of energy consumption. For example, the first condition may comprise a greater signal-to-noise ratio than the second condition, and thus the second rate of energy consumption may be greater than the first rate of energy consumption. In another example, the first condition may comprise a greater amount of motion than the second condition, and the first rate of energy consumption may be greater than the second rate of energy consumption. In yet another example, the first condition may comprise a first mode of operation and the second condition may comprise a second mode of operation, the mode of operation determining the rate of energy consumption.

As evident from the foregoing description, the methods and processes described herein may be tied to a sensory-and-logic system of one or more machines. Such methods and processes may be implemented as a computer-application program or service, an application-programming interface (API), a library, firmware, and/or other computer-program product. FIGS. 1A and 1B show one, non-limiting example of a sensory-and-logic system to enact the methods and processes described herein. However, these methods and process may also be enacted on sensory-and-logic systems of other configurations and form factors, as shown schematically in FIG. 5.

Figure 5:
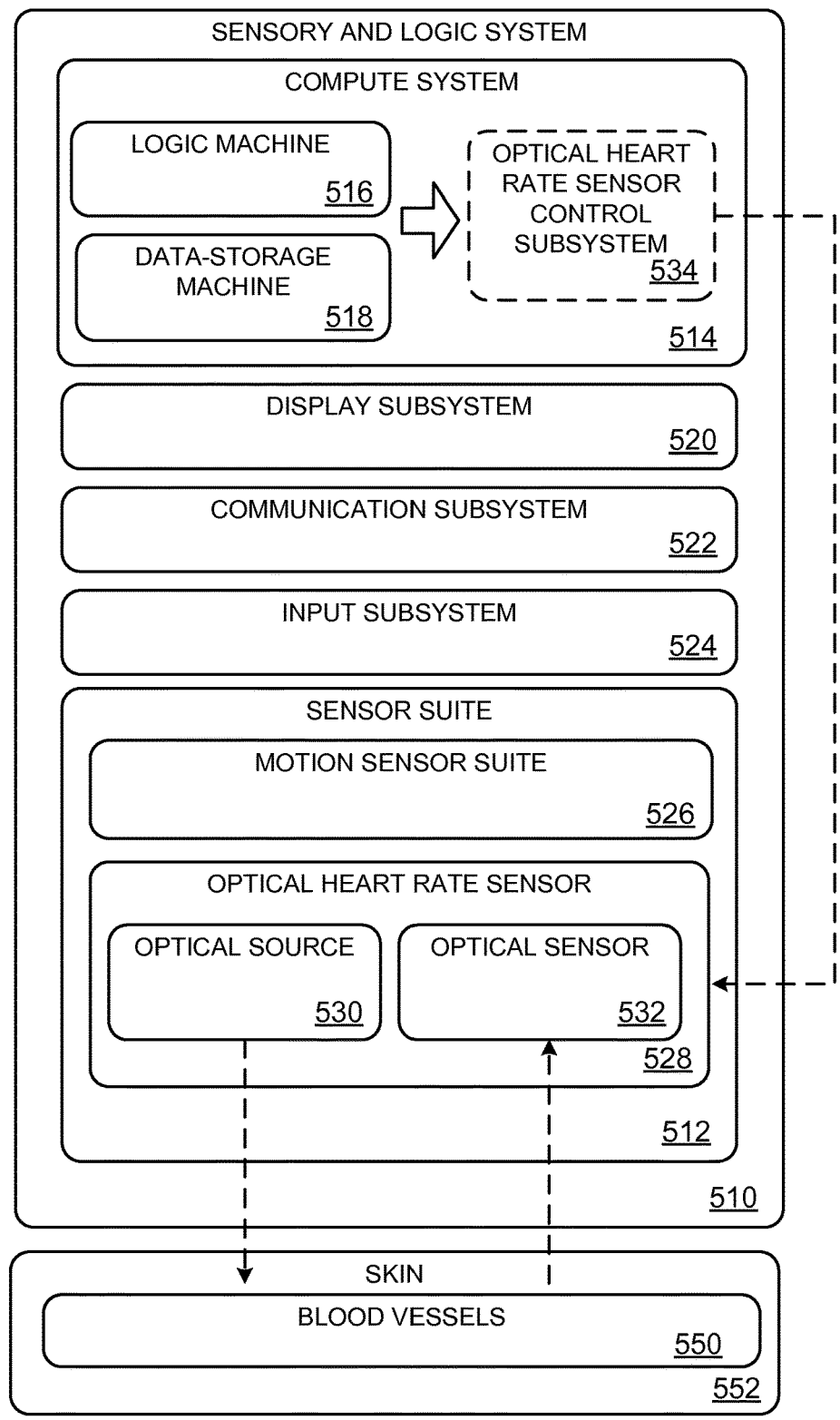
FIG. 5 schematically shows a sensory and logic system useable to dynamically change the pulsation frequency of the optical source of an optical heart rate sensor.

FIG. 5 schematically shows a form-agnostic sensory-and-logic system 510 that includes a sensor suite 512 operatively coupled to a compute system 514. The compute system includes a logic machine 516 and a data-storage machine 518. The compute system is operatively coupled to a display subsystem 520, a communication subsystem 522, an input subsystem 524, and/or other components not shown in FIG. 5.

Logic machine 516 includes one or more physical devices configured to execute instructions. The logic machine may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

Logic machine 516 may include one or more processors configured to execute software instructions. Additionally or alternatively, the logic machine may include one or more hardware or firmware logic machines configured to execute hardware or firmware instructions. Processors of the logic machine may be single-core or multi-core, and the instructions executed thereon may be configured for sequential, parallel, and/or distributed processing. Individual components of a logic machine optionally may be distributed among two or more separate devices, which may be remotely located and/or configured for coordinated processing. Aspects of a logic machine may be virtualized and executed by remotely accessible, networked computing devices in a cloud-computing configuration.

Data-storage machine 518 includes one or more physical devices configured to hold instructions executable by logic machine 516 to implement the methods and processes described herein. When such methods and processes are implemented, the state of the data-storage machine may be transformed—e.g., to hold different data. The data-storage machine may include removable and/or built-in devices; it may include optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. The data-storage machine may include volatile, nonvolatile, dynamic, static, read/write, read-only, random-access, sequential-access, location-addressable, file-addressable, and/or content-addressable devices.

It will be appreciated that data-storage machine 518 includes one or more physical devices. However, aspects of the instructions described herein alternatively may be propagated by a communication medium (e.g., an electromagnetic signal, an optical signal, etc.) that is not held by a physical device for a finite duration.

Aspects of logic machine 516 and data-storage machine 518 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

Display subsystem 520 may be used to present a visual representation of data held by data-storage machine 518. This visual representation may take the form of a graphical user interface (GUI). As the herein described methods and processes change the data held by the storage machine, and thus transform the state of the storage machine, the state of display subsystem 520 may likewise be transformed to visually represent changes in the underlying data. Display subsystem 520 may include one or more display subsystem devices utilizing virtually any type of technology. Such display subsystem devices may be combined with logic machine 516 and/or data-storage machine 518 in a shared enclosure, or such display subsystem devices may be peripheral display subsystem devices. Display 20 of FIGS. 1A and 1B is an example of display subsystem 520.

Communication subsystem 522 may be configured to communicatively couple compute system 514 to one or more other computing devices. The communication subsystem may include wired and/or wireless communication devices compatible with one or more different communication protocols. As non-limiting examples, the communication subsystem may be configured for communication via a wireless telephone network, a local- or wide-area network, and/or the Internet. Communication suite 24 of FIGS. 1A and 1B is an example of communication subsystem 522.

Input subsystem 524 may comprise or interface with one or more user-input devices such as a keyboard, mouse, touch screen, or game controller. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity. Touch-screen sensor 32 and push buttons 34 of FIGS. 1A and 1B are examples of input subsystem 524.

Sensor suite 512 may include one or more different sensors—e.g., a touch-screen sensor, push-button sensor, microphone, visible-light sensor, ultraviolet sensor, ambient-temperature sensor, contact sensors, and/or GPS receiver—as described above with reference to FIGS. 1A and 1B. Sensor suite 512 may include motion sensor suite 526. Motion sensor suite 526 may include one or more of an accelerometer, gyroscope, magnetometer, or other suitable motion detectors. Sensor suite 512 may further include optical heart rate sensor 528. As described herein, optical heart rate sensor 528 may include optical source 530 and optical sensor 532. Compute system 514 may include optical heart rate control subsystem 534, which may be communicatively coupled to logic subsystem 516 and data-storage subsystem 518. Optical source 530 may comprise one or more LED emitters, for example, while optical sensor 532 may comprise one or more photodiodes matched to detect light at frequencies that are based on the frequencies of light output by the optical source. Optical source 530 may be configured to illuminate one or more blood vessels 550 through the skin 552 of the user, and optical sensor 532 may be configured to measure illumination reflected from or transmitted through blood vessels 550.

Optical heart rate control system 534 may receive raw signals from optical sensor 532, and may further process the raw signals to determine heart rate, caloric expenditures, etc. Processed signals may be stored and output via compute system 514. Control signals sent to optical source 530 and optical sensor 532 may be based on signals received from optical sensor 532, signals derived from sensor suite 512, information stored in data-storage system 518, input received from communication subsystem 522, input received from input subsystem 524, etc.

It will be understood that the configurations and approaches described herein are exemplary in nature, and that these specific implementations or examples are not to be taken in a limiting sense, because numerous variations are feasible. The specific routines or methods described herein may represent one or more processing strategies. As such, various acts shown or described may be performed in the sequence shown or described, in other sequences, in parallel, or omitted.

The subject matter of this disclosure includes all novel and non-obvious combinations and sub-combinations of the various processes, systems and configurations, and other features, functions, acts, and/or properties disclosed herein, as well as any and all equivalents thereof.

The invention claimed is:

1. An optical heart rate sensor, comprising:
   an optical source configured to illuminate one or more blood vessels through a user's skin;
   an optical sensor configured to measure reflected illumination from the blood vessels; and
   a storage machine holding instructions executable by a logic machine to:
   determine a heart rate of the user over time based on signals output by the optical sensor;
   execute a programmed workout application having a workout schedule including two or more workout segments;
   dynamically operate the optical source and optical sensor at a first rate of energy consumption based on the workout schedule indicating that a first workout segment of the two or more workout segments has begun; and
   a period of time after completion of the first workout segment, dynamically operate the optical source and optical sensor at a second rate of energy consumption based on the workout schedule indicating that a second workout segment of the two or more workout segments has replaced the first workout segment.

2. The optical heart rate sensor of claim 1, wherein the first rate of energy consumption is greater than the second rate of energy consumption.

3. The optical heart rate sensor of claim 1, further comprising a motion sensor.

4. The optical heart rate sensor of claim 3, wherein the first workout segment comprises a greater amount of motion than the second workout segment, and the first rate of energy consumption is greater than the second rate of energy consumption, and wherein the programmed workout application being executed was selected based on signals derived from the motion sensor.

5. The optical heart rate sensor of claim 1, wherein the programmed workout application being executed was selected by the user.

6. The optical heart rate sensor of claim 1, wherein the optical source is configured to pulse on and off with a pulsation frequency and a greater rate of energy consumption corresponds with a higher pulsation frequency.

7. The optical heart rate sensor of claim 6, wherein the pulsation frequency is increased above a default pulsation frequency when the user is engaged in the second workout segment, and further increased when the user is engaged in the first workout segment.

8. The optical heart rate sensor of claim 6, wherein the pulsation frequency is decreased below a default pulsation frequency when the user is engaged in the second workout segment, and increased over the default pulsation frequency when the user is engaged in the first workout segment.

9. The optical heart rate sensor of claim 6, wherein the pulsation frequency is based on a user-defined pulsation frequency profile.

10. The optical heart rate sensor of claim 1, wherein the optical source is configured to emit light with a light intensity and a greater rate of energy consumption corresponds with a greater light intensity.

11. A method for a determining a heart rate, comprising:
    illuminating one or more blood vessels through a user's skin with an optical source configured to pulse on and off at a pulsation frequency;

measuring reflected illumination from the one or more blood vessels with an optical sensor; and dynamically adjusting the pulsation frequency of the optical source based on a downstream application, but not based on a motion signal, the downstream application configured to track a preprogrammed workout including two or more workout segments, and further configured to dynamically increase the pulsation frequency of the optical source based on receiving a signal indicating that first workout segment of the two or more workout segments has begun, and, following a period of time after completion of the first workout segment, to dynamically adjust the pulsation frequency of the optical source based on the preprogrammed workout indicating that a second workout segment of the two or more workout segments has replaced the first workout segment.

12. The optical heart rate sensor of claim 11, wherein dynamically adjusting the pulsation frequency of the optical source based on a downstream application configured to track a preprogrammed workout further comprises:

dynamically adjusting the pulsation frequency of the optical source for a data-collection window duration based on a duration of a workout segment.

13. The method of claim 11, further comprising:

pulsing the optical sensor on and off at a pulsation frequency; and dynamically adjusting the pulsation frequency of the optical sensor concurrent with dynamically adjusting the pulsation frequency of the optical source.

14. An optical heart rate sensor, comprising:

a user interface configured to receive input indicating a programmed workout including two or more segments;

an optical source configured to illuminate one or more blood vessels through a user's skin, and further configured to pulse on and off with a pulsation schedule dictated by the programmed workout, the pulsation schedule pulsing the optical source on and off at a first pulsation frequency based on receiving a signal indicating that a first segment of the two or more segments has begun and pulsing the optical source on and off at a second, different, pulsation frequency based on receiving a signal indicating that a second segment of the two or more segments has begun;

an optical sensor configured to measure illumination from the one or more blood vessels.

15. The optical heart rate sensor of claim 14, further comprising a storage machine holding instructions executable by a logic machine to:

receive a signal from the optical sensor; and increase the first pulsation frequency responsive to a signal-to-noise ratio derived from the signal received from the optical sensor decreasing below a threshold.

16. The optical heart rate sensor of claim 14, further comprising one or more motion sensors, and a storage machine holding instructions executable by a logic machine to:

receive input from a user indicating a programmed workout including two or more segments;

dynamically adjust the first pulsation frequency based on signals received from the one or motion sensors indicating whether the user is actively engaged in a segment of the programmed workout.

* * * * *